United States Patent

Schnabel et al.

[11] Patent Number: 5,936,085
[45] Date of Patent: Aug. 10, 1999

[54] PROCESS FOR THE PREPARATION OF HERBICIDAL SULFONYLUREAS AND OF N-(PYRIMIDINYL OR TRIAZINYL)-CARBAMATES AS INTERMEDIATE PRODUCTS

[75] Inventors: Gerhard Schnabel, Grosswallstadt; Harald Knorr, Frankfurt; Klemens Minn, Hattersheim; Jan Vermehren, Idstein, all of Germany

[73] Assignee: Hoechst Schering AgrEvo GmbH, Berlin, Germany

[21] Appl. No.: 08/678,127

[22] Filed: Jul. 11, 1996

[30] Foreign Application Priority Data

Aug. 2, 1995 [DE] Germany .............. 195 28 303

[51] Int. Cl.$^6$ ............... C07D 251/46; C07D 401/12; C07D 403/12; C07D 239/69
[52] U.S. Cl. ................ 544/211; 544/212; 544/206; 544/207; 544/208; 544/209; 544/197; 544/198; 544/320; 544/321; 544/323; 544/324; 544/331; 544/332
[58] Field of Search ................ 544/211, 212, 544/213, 332, 206, 207, 197, 321, 331

[56] References Cited

FOREIGN PATENT DOCUMENTS

| PS 0 187 489 | 7/1986 | European Pat. Off. . |
|---|---|---|
| PS 0 301 784 | 2/1989 | European Pat. Off. . |
| PS 0 562 575 | 9/1993 | European Pat. Off. . |
| PS 0 562 576 | 9/1993 | European Pat. Off. . |
| OS 42 36 902 | 5/1994 | Germany . |
| WO 89/10921 | 11/1989 | WIPO . |
| WO 92/00304 | 1/1992 | WIPO . |

*Primary Examiner*—John M. Ford
*Attorney, Agent, or Firm*—Frommer Lawrence & Haug

[57] ABSTRACT

Disclosed and claimed is a process for the preparation of a carbamate (IV)

$$Ar-O-CO-NR-B \quad (IV)$$

by reaction of a salt $$M^\oplus \; ^\ominus NR-B \quad (II-S)$$

with a diaryl carbonate $$(ArO)_2CO \quad (III).$$

The carbamate can be reacted, without any necessity of intermediate isolation, with a sulfonamide A—SO$_2$NH$_2$ (V) to give a sulfonylurea (I) or salts thereof $$A-SO_2-NH-CO-NR-B \quad (I).$$

And thus, disclosed and claimed too is a process for the preparation of sulfonylurea (I) by (i) contacting a salt (II-S) with a diaryl carbonate (III) to form a carbamate (IV), and (ii) contacting carbamate (IV) from step (i) with or without intermediate isolation, with a sulfonamide (V). These processes avoid the use of alkali metal hydrides as a base. And, these processes can additionally include the preparation of salt (II-S) from a compound H—NR—B (II) and base M$^\oplus$Base$^\ominus$.

13 Claims, No Drawings

PROCESS FOR THE PREPARATION OF HERBICIDAL SULFONYLUREAS AND OF N-(PYRIMIDINYL OR TRIAZINYL)-CARBAMATES AS INTERMEDIATE PRODUCTS

RELATED APPLICATIONS

Reference is made to German application 195 28 303.1, filed Aug. 2, 1995 and incorporated herein by reference. Documents cited throughout this text are also hereby incorporated herein by reference.

FIELD OF THE INVENTION

The invention relates to processes for the preparation of carbamates which are suitable for the preparation of herbicidally active sulfonylureas of the formula (I)

$$A\text{—}SO_2\text{—}NH\text{—}CO\text{—}NR\text{—}B \tag{I}$$

in which
- A is an organic radical which optionally contains heteroatoms, for example an aliphatic, aromatic or heteroaromatic radical, which is unsubstituted or substituted and is bonded directly or via a divalent group with heteroatoms to the $SO_2$ group in formula (I),
- B is a pyrimidin-2-yl or 1,3,5-triazin-2-yl radical, which is unsubstituted or substituted, and
- R is hydrogen, $C_1$–$C_5$-alkyl, $C_1$–$C_5$-haloalkyl, $C_1$–$C_5$-alkoxy or $C_1$–$C_5$-haloalkoxy.

The invention further relates to processes for preparing the sulfonylureas of the formula (I).

BACKGROUND OF THE INVENTION

Compounds of the formula (I) are known and can be employed as plant protection agents having a herbicidal action (see, for example, WO 92/00304, DE-A1-4236902, WO 89/10921, EP-A1-301784, EP-A1-187489). That is, compounds of formula (I) are sulfonylurea herbicides.

Known processes for the preparation of compounds of formula (I) often have disadvantages. For example, many of the known processes for the preparation of compounds of formula (I) obtain the compounds only in poor yields, especially if sparingly soluble heterocyclic amine components are required. Other processes are undesirably multi-stage processes or, in some cases require the use of highly toxic chemicals (such as, for example, phosgene) or of hazardous reagents (such as, for example, alkali metal hydrides), such that, for safety reasons, particular precautions must be taken when carrying out these processes on a large industrial scale. Moreover, poor yields, or having to undergo multi-stages (multi-steps or "pots"), or having to undertake particular safety precautions due to the need for using highly toxic chemicals or hazardous reagents, present increased costs. Thus there are economic disadvantages from prior processes for preparing compounds of formula (I).

Processes for obtaining the sulfonylurea herbicides of formula (I) involve the reaction of sulfonamides of the formula $A\text{—}SO_2\text{—}NH_2$ and carbamates of the formula $Ar\text{—}O\text{—}CO\text{—}NR\text{—}B$, in which Ar is an aromatic radical and A, B and R have the meanings given therefor in formula (I) (see, for example, the patent publications cited above). If the preparation of the carbamates is included in the process, this variant usually also has disadvantages because strong bases, which are difficult to handle, must be employed. For example, the "carbamate" process of EP-A-562576 for the preparation of sulfonylurea herbicides requires sodium hydride as the base. Therefore, the "carbamate" process has disadvantages which include having to undertake safety precautions due to the use of a hazardous reagent, sodium hydride, and the attendant high expenditures (costs) involved with a process involving this hazardous reagent.

Accordingly, it would be desired to provide a process for the preparation of sulfonylurea herbicidal compounds of the formula (I) which overcomes one or more of the disadvantages of prior processes. For instance, it would be desired to provide a process for the preparation of formula (I) compounds which avoids the multi-stages of previous processes, or which avoids the use of highly toxic chemicals or of hazardous reagents of prior processes. And, it would be a great advance in the art to provide a process which avoids the multi-stages and the use of highly toxic chemicals and/or hazardous reagents of prior processes.

OBJECTS AND SUMMARY OF THE INVENTION

Objects of the invention can include a novel process for the preparation of carbamates of the formula (IV) and, of using the carbamates including in a one-pot process, by which compounds of formula (I) can be prepared, by reaction of readily accessible starting materials. Objects of the invention can further include to provide, as compared with the prior art, for example, EP-A-562576, novel processes having advantages, for instance, in that the use of reagents such as alkali metal hydrides, which can be handled safely on a large industrial scale only with expensive measures, are avoided.

It has now been surprisingly found, and the invention thus provides, a process for the preparation of a carbamate of the formula (IV)

$$Ar\text{—}O\text{—}CO\text{—}NR\text{—}B \tag{IV}$$

in which
- Ar is unsubstituted or substituted aryl, preferably phenyl,
- B is a pyrimidin-2-yl or 1,3,5-triazin-2-yl radical, which is unsubstituted or substituted, and
- R is hydrogen, $C_1$–$C_5$-alkyl, $C_1$–$C_5$-haloalkyl, $C_1$–$C_5$-alkoxy or $C_1$–$C_5$-haloalkoxy, which comprises contacting under reaction conditions a compound of the formula (II)

$$H\text{—}NR\text{—}B \tag{II}$$

with a base of the formula $M^\oplus Base^\ominus$, in which $M^\oplus$ is the equivalent of a cation and $Base^\ominus$ is the anion equivalent of an oxygen base, to form a reaction mixture in which the compound of formula (II) is converted into the corresponding salt of the formula (II-S)

$$M^\oplus \phantom{}^\ominus NR\text{—}B \tag{II-S},$$

and reacting the reaction mixture with a diaryl carbonate of the formula (III) (or contacting under reaction conditions the reaction mixture with the compound of formula (III))

$$(Ar\text{—}O)_2CO \tag{III}$$

to form the carbamate of the formula (IV), wherein in the formulae (II), (II-S) and (III), the symbols Ar, B and R are defined as in formula (IV).

The carbamate (IV) obtained by the process can be intermediately isolated, or further processed directly, by customary methods.

Direct further processing of the carbonate of formula (IV) to obtain the sulfonylurea of formula (I) is surprisingly possible with good yields and, without expensive process measures such as changing the solvent or partially removing by-products or auxiliaries from the preceding process stages.

Thus, it has been surprisingly found and the invention therefore also provides, a process, preferably a "one-pot" process, for the preparation of a sulfonylurea of the formula (I) or a salt thereof, which comprises contacting under reaction conditions a compound of the formula (II)

H—NR—B　(II)

with a base of the formula $M^{\oplus}Base^{\ominus}$, in which $M^{\oplus}$ is the equivalent of a cation and $Base^{\ominus}$ is the anion equivalent of an oxygen base, to form a first reaction mixture in which the compound of formula (II) is converted into the corresponding salt of the formula (II-S)

$M^{\oplus}$ $^{\ominus}$NR—B　(II-S)

reacting the first reaction mixture with a diaryl carbonate of the formula (III) (or contacting under reaction conditions the first reaction mixture with the compound of formula (III)),

(Ar—O)$_2$CO　(III)

in which

Ar is unsubstituted or substituted aryl, preferably phenyl, whereby the carbamate of the formula (IV) is formed in a second reaction mixture

Ar—O—CO—NR—B　(IV), and contacting under reaction conditions the second reaction mixture containing the carbamate of formula (IV), or, the carbamate of formula (IV), with a sulfonamide of the formula (V), without any necessity of isolating the carbamate of formula (IV) prior to contacting within the sulfonamide of formula (V), to form a third reaction mixture,

A—SO$_2$NH$_2$　(V)

and, optionally, then isolating the compound of the formula (I) or salt thereof, from the third reaction mixture, wherein, in the formulae (II), (II-S), (IV) and (V), the symbols A, B and R are defined as in formula (I).

In even broader terms the invention provides a process for preparing a sulfonylurea of formula (I) or a salt thereof comprising contacting a salt of formula (II-S) with a diaryl carbonate of formula (III) under reaction conditions to form a reaction mixture comprising a carbamate of formula (IV) and contacting the carbamate (IV), without any necessity of intermediate isolation thereof from the reaction mixture, under reaction conditions, with a sulfonamide of formula (V).

And, in yet broader terms, the invention provides a process for preparing a carbamate of formula (IV) which comprises contacting a salt of formula (II-S) with a diaryl carbonate of formula (III) under reaction conditions.

Thus, if desired the carbamate itself can be prepared and isolated, and the isolated carbamate can then be contacted with the diaryl carbonate to obtain the sulfonylurea of formula (I) (although such intermediate isolation is not necessary and the contacting with the diaryl carbonate can be of the carbamate (IV) without any intermediate isolation, e.g., of the reaction mixture in which the carbamate is formed).

These and other objects and embodiments of the invention are disclosed in or are obvious from the following Detailed Description.

DETAILED DESCRIPTION

The processes according to the invention (the carbamate process and the one-pot process) are carried out by first deprotonating the heterocyclic amines of the formula (II) with suitable oxygen bases $M^{\oplus}Base^{\ominus}$ (oxides, hydroxides, carbonates or alcoholates) in a solvent to form the salt (II-S).

Suitable salts of oxygen bases $M^{\oplus}Base^{\ominus}$ are, for example, salts from the group consisting of alkali metal oxides, alkaline earth metal oxides, alkali metal hydroxides, for example NaOH and KOH, alkaline earth metal hydroxides, tetraalkylammonium hydroxides, alkali metal alcoholates, for example sodium ethylate, sodium methylate, potassium ethylate, potassium methylate, sodium isopropylate, potassium isopropylate, sodium tert-butylate, potassium tert-butylate and similar branched alcoholates, and alkaline earth metal alcoholates, preferably alkali metal alcoholates of sodium and potassium.

Suitable solvents are those which are capable of dissolving or at least partly dissolving the reactants at the temperatures chosen. The suitable solvents can easily be ascertained without undue experimentation, by the skilled artisan, from this disclosure and the knowledge in the art. Organic solvents which are inert under the reaction conditions, especially aprotic dipolar solvents and mixtures thereof, are of particular interest.

Examples of solvents which are suitable are:

ethers, such as diethyl ether, tetrahydrofuran (THF), dioxane, diglyme and tetraglyme, amides, such as dimethylformamide (DMF), dimethylacetamide (DMA) and N-methylpyrrolidone, ketones, such as acetone, nitrites, such as acetonitrile, propionitrile, butyronitrile and benzonitrile, sulfoxides and sulfones, such as dimethylsulfoxide (DMSO) and sulfolane, halogenated aliphatic and aromatic hydrocarbons, such as methylene chloride and chlorobenzene.

The formation of the salt (II-S) can be carried out in a wide temperature range, which may be limited in an individual case by the melting point or boiling point of the solvent used and the dissolving properties thereof. The temperature of the salt formation is preferably in the range from about −40° C. up to about the boiling point of the particular solvent, more preferably in the range from about −20° C. up to about the boiling point of the particular solvent; for instance, from about −10° C. to about +100° C.

The reactive anion in the salt (II-S) of the heterocyclic amine is then preferably reacted without intermediate isolation with a diaryl carbonate (III), such as, for example, diphenyl carbonate, to give the corresponding carbamate (IV). This reaction can be carried out in a wide temperature range, depending on the solvent; and, can be effected, for example, at temperatures from about −40 to about +180° C., preferably from about −20 to about +150° C., more preferably from about −10 to about 100° C., and especially from about 0 to about 100° C.

For carrying out the reaction of the anion (II-S) and the diaryl carbonate (III), the addition of a drying agent, for example a molecular sieve (e.g., about 3 Å to about 5 Å, preferably about 3 Å or about 4 Å), or the addition of phase transfer catalysts, for example polyethylene glycol ethers, organic ammonium salts, crown ethers, and the like, may be advantageous.

The carbamate (IV) can then be isolated without undue experimentation from this disclosure and by knowledge of customary methods, for example combined gentle methods, such as filtration of the solution, evaporation on a rotary evaporator, recrystallization, extraction at various pH values, chromatography, and the like. 4-Methoxy-6-methyl-2-phenoxycarbonylamino-1,3,5-triazine, for example, can thus be obtained in a satisfactory purity and yield ($^1$H-NMR (200 Mhz, D$_6$-DMSO): δ ppm=8.5 (s,1H), 7.4 (m,2H), 7.2 (m,3H), 4.05 (s,3H)).

The optimum ratios of the components of heterocyclic amine (II), base M$^\oplus$Base$^\ominus$ and diaryl carbonate (III) can vary from case to case, and can be determined by the skilled artisan for any particular case, without undue experimentation, on the basis of this disclosure.

For example, the base is expediently employed in an equimolar amount or in excess in relation to the amine (II), for instance, in a molar ratio of about 1:1 to about 5:1, preferably about 1:1 to about 3:1. The diaryl carbonate (III) is employed, for example, in an equimolar amount, in excess, or in a deficit, in relation to the amine (II); preferably in a molar ratio of about 1:2 to about 2:1, and more preferably in a molar ratio of about 1:1.5 through about 1.5:1.

In the one-pot process according to the invention, the carbamate (IV) is intermediately formed and reacted with the sulfonamide of the formula (V), without intermediate isolation (or without any necessity of intermediate isolation). The reaction temperatures can be from about −40 to about 180° C., preferably from about −20 to about 150° C., and especially from about 0 to about 80° C.

When the reaction has ended, the sulfonylureas of the formula (I) or salts (I-S) thereof can optionally be isolated without undue experimentation from this disclosure and by knowledge of customary purification steps.

To isolate neutral sulfonylureas, for example, the reaction mixture is filtered and the filtrate is then poured cautiously into a dilute aqueous acid, such as, for example, dilute hydrochloric acid or formic acid, whereby the product separates out. After the product has separated out, it can then be washed—for instance with water and/or one or more organic solvents (for example alcohols, such as methanol, ethanol and isopropanol; ethers, such as diethyl ether and tert-butyl methyl ether; ketones, such as acetone; esters, such as ethyl acetate and methyl acetate)—and dried, whereby the desired products can be obtained in good yields and good purities (as a rule more than about 90% pure).

Alternatively, to isolate the sulfonylureas of formula (I), the reaction mixture is filtered and the filtrate is introduced into a two-phase system of an organic solvent, such as, for example, toluene, tert-butyl methyl ether, methyl acetate or ethyl acetate, and dilute aqueous acid, whereby the product separates out. The sulfonylurea which has separated out is then obtained directly, again with good purities and yields.

To isolate the salts of the sulfonylureas of the formula (I), the product of the reaction is isolated without first acidifying the reaction mixture. The salts of the sulfonylureas of the formula (I) then can be isolated, for example, by the following route:

When the reaction has ended and the mixture has been filtered, a non-polar organic solvent is added to the filtrate in order to lower the solubility of the salt in the reaction mixture. Alternatively, the reaction mixture can be concentrated by distilling off volatile components. The sulfonylurea salt which has then separated out can be purified, for example, by stirring with an organic solvent, such as, for example, methanol, diethyl ether, ethyl acetate, methyl acetate, ethanol, tert-butyl methyl ether or a solvent mixture.

For carrying out the reaction of the carbamate (IV) and the sulfonamide (V), the addition of a drying agent, for example a molecular sieve (e.g., about 3 Å to about 5 Å, preferably about 3 Å or about 4 Å) or the addition of phase transfer catalysts, for example polyethylene glycol ethers, organic ammonium salts, crown ethers, and the like, may be advantageous from case to case.

The ratio of the components of sulfonamide (V), diaryl carbonate (III), heterocyclic amine (II) and base M$^\oplus$Base$^\ominus$ can vary from case to case, and can be determined by the skilled artisan for any particular case, without undue experimentation, on the basis of this disclosure. Preferably, the molar ratio of the amounts of sulfonamide (V) and components of the formula (III) or (II) is from about 1:0.8 through about 1:3.5, preferably from about 1:1 to about 1:2.

In formula (I) and all the formulae, the alkyl, alkoxy, haloalkyl, haloalkoxy, alkylamino and alkylthio radicals and the corresponding unsaturated and/or substituted radicals can in each case be straight-chain or branched in the carbon skeleton. Unless specifically stated, the lower carbon skeletons can have 1 to 6 carbon atoms and unsaturated groups, can have 2 to 6 carbon atoms; and, these are preferred for these radicals.

Halogen is, for example, fluorine, chlorine, bromine or iodine. Haloalkyl, -alkenyl and -alkynyl are alkyl, alkenyl and alkynyl respectively which are partly or completely substituted by halogen, preferably by fluorine, chlorine and/or bromine, more preferably by fluorine or chlorine.

An aromatic carbocyclic radical (=aryl) is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic; it preferably contains one or more heteroatoms in the ring, which also include substituted heteroatoms, preferably selected from the group consisting of N, O, S, So and SO$_2$; for example, it is an aliphatic heterocyclyl radical having 3 to 7 ring atoms or a heteroaromatic radical having 5 or 6 ring atoms, and contains 1, 2 or 3 hetero units or heteroatoms. The heterocyclic radical can be, for example, a heteroaromatic radical or ring (heteroaryl), such as, for example, a mono-, bi- or polycyclic aromatic system, in which at least 1 ring contains one or more heteroatoms, for example pyridyl, pyrimidinyl, pyridazinyl, pyrazinyl, thienyl, thiazolyl, oxazolyl, furyl, pyrrolyl, pyrazolyl and imidazolyl, or is a partly or completely hydrogenated radical, such as oxiranyl, pyrrolidyl, piperidyl, piperazinyl, dioxolanyl, morpholinyl and tetrahydrofuryl.

Possible substituents for a substituted aromatic or heteroaromatic radical are, for example:

One or more, preferably 1, 2 or 3, radicals selected from the group consisting of halogen, alkyl, haloalkyl, alkoxy, haloalkoxy, alkylthio, hydroxy, amino, nitro, carboxyl, cyano, azido, alkoxycarbonyl, alkylcarbonyl, formyl, carbamoyl, mono- and dialkylaminocarbonyl, substituted amino, such as acylamino and mono- and dialkylamino, and alkylsulfinyl, haloalkylsulfinyl, alkylsulfonyl and haloalkylsulfonyl; the term "substituted radicals", such as substituted aryl and the like, includes as substituents, in addition to the saturated hydrocarbon-containing radicals mentioned, corresponding unsaturated aliphatic and aromatic radicals, such as optionally substituted alkenyl, alkynyl, alkenyloxy, alkynyloxy, phenyl, phenoxy and the like. In the case of radicals with carbon atoms, those having 1 to 4 carbon atoms, in particular 1 or 2 carbon atoms, are preferred. Substituents from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano are as a rule preferred. The substituents methyl, methoxy and chlorine are particularly preferred.

Compounds of the formula (II) which are suitable for the process according to the invention are primary or secondary aminopyrimidines and -triazines, where the heterocyclic rings can be unsubstituted or substituted. Typical amines are, for example, compounds of the formula (IIa)

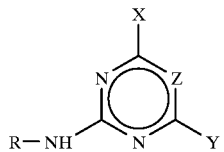

(IIa)

in which

R is hydrogen, $C_1$–$C_5$-alkyl, $C_1$–$C_5$-haloalkyl, $C_1$–$C_5$-alkoxy or $C_1$–$C_5$-haloalkoxy, preferably hydrogen or $C_1$–$C_4$-alkyl, X and Y independently of one another are hydrogen, halogen, $C_1$–$C_6$-alkyl, $C_1$–$C_6$-alkoxy, $C_1$–$C_6$-alkylthio, mono- or di-($C_1$–$C_4$-alkyl)amino, where each of the last six radicals mentioned is unsubstituted in the alkyl part or substituted by one or more radicals from the group consisting of halogen, $C_1$–$C_4$-alkoxy, $C_1$–$C_4$-haloalkoxy and $C_1$–$C_4$-alkylthio, or $C_3$–$C_6$-cycloalkyl, $C_2$–$C_6$-alkenyl, $C_2$–$C_6$-alkynyl, $C_2$–$C_6$-alkenyloxy or $C_1$–$C_6$-alkynyloxy and Z is CH or N.

Substituted or unsubstituted diaryl carbonates of the formula (III), in particular diphenyl carbonates, are suitable as the reagent for the process according to the invention. Preferred compounds correspond to the formula (IIIa) (and, from formula (IIIa), preferred phenyl radicals for Ar or aryl in the formulae in this disclosure are also provided)

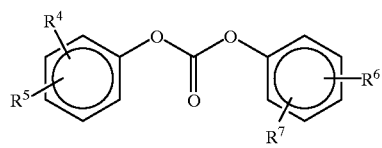

(IIIa)

in which $R^4$, $R^5$, $R^6$ and $R^7$ independently of one another are hydrogen, halogen, $C_1$–$C_4$-alkyl, $C_1$–$C_4$-haloalkoxy, $C_1$–$C_4$-haloalkyl, $C_1$–$C_4$-alkoxy, nitro or CN.

Preferred aromatic or heteroaromatic sulfonamides of the formula A—$SO_2NH_2$ (V) are compounds of the formulae (Va) to (Ve) (and, from formulae (Va) to (Ve) preferred aromatic or heteroaromatic moieties for A are provided)

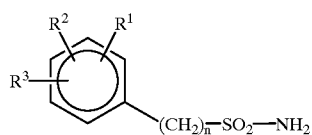

(Va)

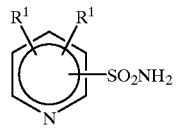

(Vb)

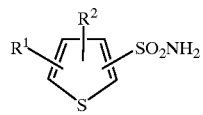

(Vc)

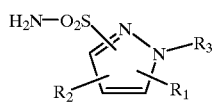

(Vd)

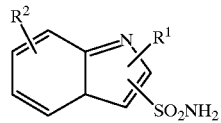

(Ve)

in which n is 0 or 1, $R^1$ is H, OH, $CO_2H$, $CONH_2$, halogen, CN, $NO_2$, $NH_2$, $SO_2NH_2$, $C_1$–$C_6$-alkyl, $C_2$–$C_6$-alkenyl, $C_2$–$C_6$-alkynyl, $C_3$–$C_7$-cycloalkyl, $C_4$–$C_{10}$-cycloalkylalkyl, $C_1$–$C_6$-alkoxy, $C_2$–$C_6$-alkenoxy, $C_2$–$C_6$-alkinoxy, $C_3$–$C_7$-cycloalkoxy, $C_4$–$C_{10}$-cycloalkylalkoxy, mono- oder di-($C_1$–$C_4$-alkyl)amino, $C_1$–$C_6$-alkylthio, $C_1$–$C_6$-alkylsulfinyl, $C_1$–$C_6$-alkylsulfonyl, $C_2$–$C_6$-alkenylsulfinyl, $C_2$–$C_6$-alkenylsulfonyl, $C_2$–$C_6$-alkanylthio, $C_2$–$C_6$-alkynylthio, $C_2$–$C_6$-alkynylsulfinyl, $C_2$–$C_6$-alkynylsulfonyl, $C_3$–$C_7$-cycloalkylsulfonyl, $C_4$–$C_9$-cycloalkylalkylsulfonyl, $C_1$–$C_6$-alkoxycarbonyl, $C_2$–$C_6$-alkenoxycarbonyl, $C_2$–$C_6$-alkinoxycarbonyl, $C_3$–$C_7$-cycloalkoxycarbonyl, mono- or di-($C_1$–$C_4$-alkyl(aminocarbonyl or mono- or di-($C_1$–$C_4$-alkyl)aminosulfonyl, where each of the last 31 radicals mentioned is unsubstituted or substituted by one or more radicals from the group consisting of halogen, CN, OH, $NH_2$, $NO_2$, $NHCH_3$, $N(CH_3)_2$, $C_1$–$C_3$-alkoxy, $C_1$–$C_3$-haloalkoxy, $C_1$–$C_3$-alkylthio, $C_1$–$C_3$-haloalkylthio, phenyl, $COOCH_3$, $COOC_2H_5$, $CONH_2$, $CONHCH_3$, $CON(CH_3)_2$, $SO_2CH_3$, $SO_2C_5$, $SOCH_3$ and $SOC_2H_5$, $R^2$ is H, OH, $NH_2$, mono- or di-($C_1$–$C_4$-alkyl)amino, $C_1$–$C_4$-alkoxy, $C_2$–$C_4$-alkenoxy, $C_2$–$C_4$-alkinoxy, where the last 5 radicals mentioned are unsubstituted or substituted by one or more radicals from the group consisting of halogen, CN, $C_1$–$C_3$-haloalkyl, $C_1$–$C_3$-alkoxy and $C_1$–$C_3$-haloalkoxy, or NR'R", $CH_2$NR'R", halogen, CN, $NO_2$ or heterocyclyl, in which R' is H, OH, $C_1$–$C_6$-alkyl, $C_1$–$C_5$-alkoxy, $C_3$–$C_7$-cycloalkyl or $C_4$–$C_8$-cycloalkylalkyl, where the last 4 radicals mentioned are unsubstituted or substituted by one or more radicals from the group consisting of halogen, $C_1$–$C_3$-haloalkyl, $C_1$–$C_3$-alkoxy and $C_1$–$C_3$-haloalkoxy, and R" is an acyl radical, such as, for example, CO—$NH_2$, CHO, $C_1$–$C_6$-alkylcarbonyl, $C_1$–$C_6$-alkoxycarbonyl, $C_3$–$C_7$-cycloalkylcarbonyl, $C_4$–$C_9$-cycloalkylcarbonyl, $C_3$–$C_7$-cycloalkoxycarbonyl, $C_4$–$C_9$-cycloalkylalkoxycarbonyl, $C_1$–$C_6$-alkylsulfonyl, mono- or di-($C_1$–$C_4$-alkyl)aminocarbonyl or mono- or di-($C_1$–$C_4$-alkyl)aminosulfonyl, where each of the last 11 radicals mentioned is unsubstituted or substituted by one or more radicals from the group consisting of halogen, $C_1$–$C_3$-alkoxy and $C_1$–$C_3$-haloalkoxy, or NR'R" is a substituted or unsubstituted hydrazine radical and $R^3$ is H, halogen, $C_1$–$C_3$-alkyl, $C_1$–$C_3$-haloalkyl, $C_1$–$C_3$-alkoxy, $C_1$–$C_3$-haloalkoxy, $NH_2$, $NHCH_3$, $N(CH_3)_2$, $NO_2$ or CN.

The processes according to the invention, without necessarily wishing to be bound by any one particular theory, is summarized in the following equation 1, by the example of certain pyrimidines and triazines of the formula (II).

Equation 1

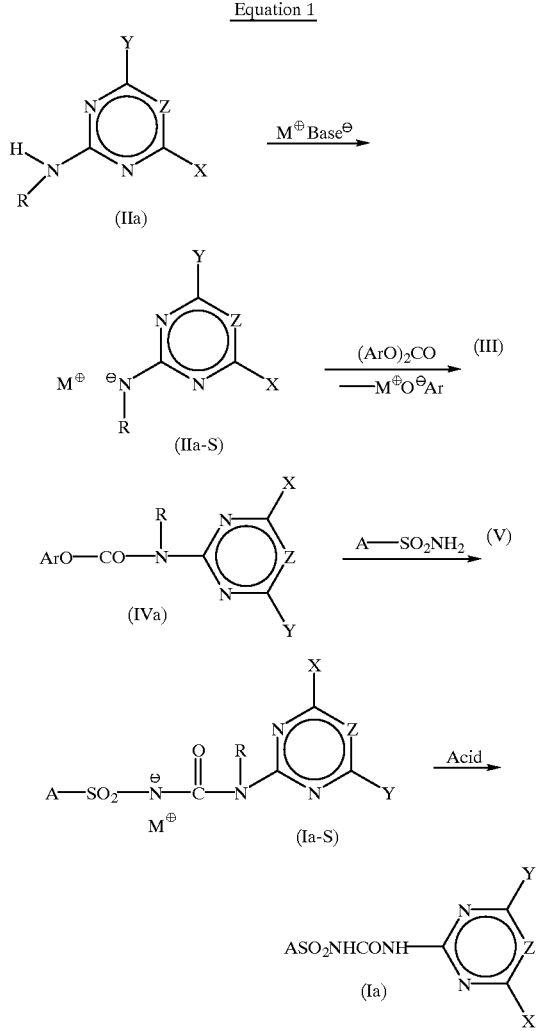

For synthesis of sulfonylureas of the formula (I) by the process according to the invention, the above mentioned disadvantages, such as, for example, the use of highly toxic or hazardous chemicals (for example phosgene or alkali metal hydrides, such as sodium hydride) are avoided. Furthermore, sparingly soluble heterocyclic amines—such as, for example, 2-amino-4-methoxy-6-methyltriazine—can also be converted into sulfonylureas in very good yields by the process of the invention.

Additionally, with respect to sulfonylureas and their uses as herbicides and in herbicidal formulations, reference is made to U.S. application Ser. Nos. 07/859,513, filed Jun. 8, 1992 and 08/224,324, filed Apr. 7, 1994, incorporated herein by reference. From those applications, one skilled in the art can devise products and reactants for use in the processes of the invention, and can use products of the processes of the invention as herbicides or to formulate herbicidal formulations, without any undue experimentation.

The following non-limiting Examples are given by way of illustration only and are not to be considered a limitation of this invention.

EXAMPLES

In the following examples, the amounts data and ratios of amounts (such as percentage data) are based on the weight, if no other definitions are given.

Example 1

Methyl 2-[[[[(4-methoxy-6-methyl-1,3,5-triazin-2-yl)-amino]-carbonyl]-amino]-sulfonyl]-4-iodobenzoate.

2.85 g of 2-amino-4-methoxy-6-methyl-1,3,5-triazine was initially introduced into 40 ml of dimethylacetamide (DMA), and 2.22 g of sodium tert-butylate was then added to form a first mixture. After the first mixture was stirred for 30 minutes, it was cooled to 5° C. and 4.94 g of diphenyl carbonate was added to form a second mixture. After the second mixture was stirred at room temperature for 1 hour, it was added dropwise to a solution of 5.00 g of methyl 2-amino-sulfonyl-4-iodobenzoate (92.5% pure) and 15 ml of DMA at 0° C. to form a third mixture. After the third mixture was stirred at room temperature for 2 hours, solids were separated off by filtration. The filtrate was introduced into a mixture of 200 ml of ice-water and 10 ml of concentrated hydrochloric acid whereby the urea separated out. The urea which separated out was washed with water, methanol and diisopropyl ether and then dried. The desired sulfonylurea was thus obtained in a yield of 70% (5.2 g; purity: 93.3% (HPLC)); $^1$H-NMR ($D_6$-DMSO, 200 MHz) δ (ppm)=12.6 (s, 1H), 11.2 (s, 1H), 8.4 (d, 1H), 8.2 (dd, 1H), 7.6 (d, 1H), 4.0 (s, 3H), 3.8 (s, 3H), 2.5 (s, 3H).

This Example demonstrates that the carbamate of formula (IV) can be formed and converted, without isolation, to the sulfonylurea of formula (I), in a good yield and with high purity (of both (IV) and (I)), without using an alkali metal hydride or phosgene.

Example 2

Methyl 2-[[[[(4-methoxy-6-methyl-1,3,5-triazin-2-yl)-amino]-carbonyl]-amino]-sulfonyl]-4-iodobenzoate.

2.59 g of potassium tert-butylate was added to a suspension of 2.85 g of 2-amino-4-methoxy-6-methyl-1,3,5-triazine in 40 ml of dimethylacetamide (DMA) at room temperature to form a first mixture. A solution of 4.94 g of diphenyl carbonate in 20 ml of DMA was then added dropwise to the first mixture at about 5° C. to form a second mixture. The second mixture was subsequently added dropwise to a solution of 5.00 g of methyl 2-aminosulfonyl-4-iodobenzoate (92.5% pure) in 15 ml of DMA at about 5° C., to form a third mixture. When the reaction ended, the third mixture was filtered over kieselguhr (®Celite). The filtrate was introduced into a solution of 200 ml of ice-water and 10 ml of concentrated hydrochloric acid, whereby the crude urea product separated out. The crude product which separated out was then purified by stirring with methanol and diisopropyl ether and dried. The yield was 4.50 g (66% of theory).

This Example also demonstrates that the carbamate of formula (IV) can be formed and converted, without isolation, to the sulfonylurea of formula (I), in a good yield (of both (IV) and (I)), without using an alkali metal hydride or phosgene.

Example 3

Methyl 2-[[[[(4-methoxy-6-methyl-1,3,5-triazin-2-yl)-amino]-carbonyl]-amino]-sulfonyl]-4-iodobenzoate.

0.96 g of sodium tert-butylate was added to a suspension of 1.05 g of 2-amino-4-methoxy-6-methyl-1,3,5-triazine in 20 ml of dimethylacetamide (DMA) at room temperature, with vigorous stirring, to form a first mixture. A solution of 1.12 g of diphenyl carbonate in 10 ml of DMA was then added to the first mixture, in the course of 7 minutes, while it was cooled in an ice bath, to form a second mixture. The second mixture was subsequently stirred for another 15 minutes while cooled in the ice bath, and a solution of 1.84 g of methyl 2-aminosulfonyl-4-iodobenzoate (92.5% pure) in DMA was then added dropwise in the course of 7 minutes. When the reaction ended, the product was worked up as described in Example 1. 1.47 g of the desired product (58% of theory) was thus obtained.

This Example further demonstrates that the carbamate of formula (IV) can be formed and converted, without isolation, to the sulfonylurea of formula (I), in a good yield (of both (IV) and (I)), without using an alkali metal hydride or phosgene.

Example 4

Methyl 2-[[[[(4-methoxy-6-methyl-1,3,5-triazin-2-yl)amino]carbonyl]amino]sulfonyl]-4-iodobenzoate.

5.09 g of sodium tert-butylate was added to a suspension of 3.69 g of 2-amino-4-methoxy-6-methyl-1,3,5-triazine in 100 ml of DMA at room temperature. After cooling to 3–7° C., a solution of 5.64 g of diphenyl carbonate and 50 ml of DMA was added dropwise, to form a reaction mixture. The reaction mixture was then stirred at that temperature for 15 minutes. The reaction mixture was then added dropwise to a solution of 8.85 g of methyl 2-aminosulfonyl-4-iodobenzoate and 50 ml of DMA at 3–7° C., to form a resulting mixture which was stirred at 3° C. for 1 hour and at room temperature for 2 hours. The volatile components were then distilled off under reduced pressure. The residue was dissolved in 250 ml of water and acidified with concentrated hydrochloric acid (pH=2-3) whereby the crude product separated out. The crude product which separated out was washed with methanol and diisopropyl ether. After drying, 8.4 g of the desired product (purity>92%) was obtained.

This Example additionally demonstrates that the carbamate of formula (IV) can be formed and converted, without isolation, to the sulfonylurea of formula (I), with high purity, (of both (IV) and (I)) without using an alkali metal hydride or phosgene.

Example 5

Methyl 2-[[[(4-chloro-6-methoxypyrimidin-2-yl)amino]carbonyl]amino]sulfonyl]-benzoate.

2.03 g of sodium tert-butylate was added to a suspension of 1.68 g of 2-amino-4-chloro-6-methoxypyrimidine in 30 ml of DMA to form a reaction mixture. The reaction mixture was stirred at room temperature for 30 minutes. The reaction mixture was then added dropwise to a solution of 1.68 g of diphenyl carbonate and 25 ml of DMA at 3–7° C., to form a resulting mixture which was allowed to come slowly to room temperature. The resulting mixture was then metered into a solution of 2.03 g of methyl 2-aminosulfonylbenzoate and 20 ml of DMA at 3–7° C., which was then stirred at this temperature for 2 hours, and concentrated under reduced pressure to yield a residue. The residue was taken up in water, tert-butyl methyl ether was added, and the mixture was then acidified with concentrated hydrochloric acid, whereby a solid precipitated out. The solid which precipitated out was separated off, washed with tert-butyl methyl ether and dried. 2.36 g of the desired compound (purity>90%) was thus obtained; $^1$H-NMR (D$_6$-DMSO, 200 MHz) δ (ppm)=12.0 (s, 1H), 10.9 (s, 1H), 8.2 (m, 1H), 7.8 (m, 3H), 6.9 (s, 1H), 4.0 (s, 3H), 3.8 (s, 3H).

This Example too demonstrates that the carbamate of formula (IV) can be formed and converted, without isolation, to the sulfonylurea of formula (I), in a highly pure form (of both (IV) and (I)), without using an alkali metal hydride or phosgene.

Comparison Example

Methyl 2-[[[[(4-methoxy-6-methyl-1,3,5-triazin-2-yl)-amino]-carbonyl]-amino]-sulfonyl]-4-iodobenzoate.

0.084 g of sodium hydride (60% pure in paraffin oil) was added to a suspension of 0.23 g of 2-amino-4-methoxy-6-methyl-1,3,5-triazine in 3 ml of dimethylacetamide (DMA) at room temperature to form a mixture. The mixture was stirred until the evolution of gas ended. A solution of 0.44 g of diphenyl carbonate in 1 ml of DMA was then slowly added dropwise at about 5° C., and the resulting mixture therefrom was stirred for 10 minutes. A solution of 0.68 g of methyl 2-aminosulfonyl-4-iodobenzoate (92.5% pure) in 2 ml of DMA was slowly added dropwise, to the resulting mixture, while cooled in an ice bath, to form a reaction mixture. When the reaction ended, the reaction mixture was then introduced into a solution of 30 ml of ice-water and 0.25 ml of concentrated hydrochloric acid, whereby a crude product separated out. The crude product which separated out was then purified by washing with a little water, methanol and diisopropyl ether and drying. The yield was 0.47 g (46% of theory).

As can be seen from this Comparison Example and the foregoing Examples 1 to 5 of the present invention, the present invention, obtains better yields of the sulfonylurea of formula (I) (higher percentage of theory), in highly pure form (purity greater than 90% and greater than 92%), without having to use an alkali metal hydride (or phosgene). Such yields and purity from the present invention are surprising and unexpected. One would not expect such yields and purity in a process which avoids the use of alkali metal hydrides and phosgene, and in which it is not necessary to isolate the carbamate intermediate. The Comparison Examples, and Examples 1 to 5 also show the surprising superiority of the carbamate process of the invention (the high yield and purity of the ultimate sulfonylurea are a reflection of the superiority of the carbamate process of the invention; and, this superiority, without using an alkali metal hydride or phosgene is unexpected).

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A process for the preparation of sulfonylurea of formula (I)

A—SO₂—NH—CO—NR—B (I)

or a salt thereof, comprising:

(i) contacting a compound of the formula (II)

H—NR—B (II)

with a base M⊕Base⊖ to convert the compound of formula (II) into the corresponding salt of the formula (II-S)

(II-S) M⊕ ⊖NR—B (ii) contacting a salt of formula (II-S) with a diaryl carbonate of the formula (III)

(ArO)₂ CO (III)

to form a carbamate of formula (IV),

Ar—O—CO—NR—B (IV)

and (iii) contacting the carbamate (IV), without any necessity of intermediate isolation thereof, with a sulfonamide of formula (V)

A—SO₂NH₂ (V)

wherein

A is an organic radical, which optionally contains heteroatom(s) selected from the group consisting of N, O, SO, and SO₂, B is a pyrimidin-2-yl or 1,3,5-triazin-2-yl radical, which is unsubstituted or substituted, R is hydrogen, $C_1$–$C_5$-alkyl, $C_1$–$C_5$-haloalkyl, $C_1$–$C_5$-alkoxy or $C_1$–$C_5$-haloalkoxy, M⊕ is the equivalent of a cation, Ar is unsubstituted or substituted aryl, and Base⊖ in the anion equivalent of an oxygen base.

2. A process for the preparation of sulfonylurea of formula (I)

A—SO₂—NH—CO—NR—B (I)

or a salt thereof, comprising;

(i) contacting a salt of formula (II-S)

(II-S) M⊕ ⊖NR—B with a diaryl carbonate of the formula (III)

(ArO)₂ CO (III)

to form a carbamate of formula (IV)

Ar—O—CO—NR—B (IV)

and (ii) contacting the carbamate (IV), without any necessity of intermediate isolation thereof, with a sulfonamide of formula (V)

A—SO₂NH₂ (V)

wherein

A is an organic radical, which optionally contains heteroatom(s) selected from the group consisting of N, O, SO, and SO₂, B is a pyrimidin-2-yl or 1,3,5-triazin-2-yl radical, which is unsubstituted or substituted, and R is hydrogen, $C_1$–$C_5$-alkyl, $C_1$–$C_5$-haloalkyl, $C_1$–$C_5$-alkoxy or $C_1$–$C_5$-haloalkloxy, M⊕ is the equivalent of a cation, and Ar is unsubstituted or substituted aryl.

3. The process of claim 2 wherein in step (ii), the contacting of the carbamate (IV) with the sulfonamide (V) includes isolating the compound of formula (IV) prior thereto.

4. The process of claim 1 wherein in step (iii) the contacting of the carbamate (IV) with the sulfonamide (V) includes isolating the compound of formula (IV) prior thereto.

5. The process as claimed in claim 1, wherein a compound of the formula (IIa)

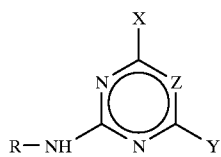

(IIa)

in which

R is hydrogen, $C_1$–$C_5$-alkyl, $C_1$–$C_5$-haloalkyl, $C_1$–$C_5$-alkoxy or $C_1$–$C_5$-haloalkoxy, X and Y independently of one another are hydrogen, halogen, $C_1$–$C_6$-alkyl, $C_1$–$C_6$-alkoxy, $C_1$–$C_6$-alkylthio, mono- or di- ($C_1$–$C_4$-alkyl) amino, where each of the last six radicals mentioned is unsubstituted in the alkyl part or substituted by one or more radicals from the group consisting of halogen, $C_1$–$C_4$-alkoxy, $C_1$–$C_4$-haloalkoxy and $C_1$–$C_4$-alkylthio, or $C_3$–$C_6$-cycloalkyl, $C_2$–$C_6$-alkenyl, $C_2$–$C_6$-alkynyl, $C_2$–$C_6$-alkenyloxy or $C_2$–$C_6$-alkynyloxy and Z is CH or N, is employed as the compound of the formula (II).

6. A process as claimed in claim 2, 1 or 5, wherein a compound of the formula (IIIa)

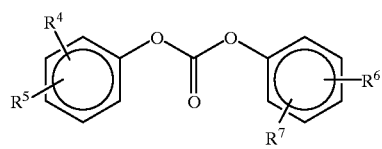

(IIIa)

in which $R^4$, $R^5$, $R^6$ and $R^7$ independently of one another are hydrogen, halogen, $C_1$–$C_4$-alkyl, $C_1$–$C_4$-haloalkoxy, $C_1$–$C_4$-haloalkyl, $C_1$–$C_4$-alkoxy or CN, is employed as the compound of the formula (III).

7. The process as claimed in claim 1 wherein a salt of an alkali metal alcoholate is employed as the base M⊕Base⊖.

8. The process as claimed in claim 7, wherein the salt of an alkali metal alcoholate is in an aprotic dipolar solvent.

9. The process as claimed in claim 8, wherein the contacting of the compound of formula (II) with the base is at a temperature of from about −40° C. up to about the boiling point of the solvent.

10. The process as claimed in claim 1 wherein in step (ii), the contacting to form the carbamate of the formula (IV) is carried out at a temperature from about −40 to about 180° C.

11. The process as claimed in claim 1, wherein step (iii) is carried out at a temperature from about −40 to about 180° C.

12. The process of claim 2 wherein in step (ii), the contacting of the carbamate (IV) with the sulfonamide (V) is without isolating the compound of formula (IV) prior thereto.

13. The process of claim 1 wherein in step (iii), the contacting of the carbamate (IV) with the sulfonamide (V) is without isolating the compound of formula (IV) prior thereto.

* * * * *